(12) United States Patent
Bloom et al.

(10) Patent No.: US 11,078,140 B2
(45) Date of Patent: Aug. 3, 2021

(54) PROCESS FOR PRODUCING 1,3-BUTANEDIOL AND FOR OPTIONALLY FURTHER PRODUCING (R)-3-HYDROXYBUTYL (R)-3-HYDROXYBUTYRATE

(71) Applicant: Archer Daniels Midland Company, Decatur, IL (US)

(72) Inventors: Paul D. Bloom, Forsyth, IL (US); Chi-Cheng Ma, Champaign, IL (US); Kevin J. Martin, Mt. Zion, IL (US); Brennan Smith, Decatur, IL (US)

(73) Assignee: ARCHER DANIELS MIDLAND COMPANY, Decatur, IL (US)

( * ) Notice: Subject to any disclaimer, the term of this patent is extended or adjusted under 35 U.S.C. 154(b) by 0 days.

(21) Appl. No.: 17/008,640

(22) Filed: Sep. 1, 2020

(65) Prior Publication Data
US 2020/0399192 A1 Dec. 24, 2020

Related U.S. Application Data

(63) Continuation of application No. 16/066,758, filed as application No. PCT/US2016/065592 on Dec. 8, 2016.

(60) Provisional application No. 62/275,284, filed on Jan. 6, 2016.

(51) Int. Cl.
*C07C 29/149* (2006.01)
*B01J 23/72* (2006.01)
*B01J 25/00* (2006.01)
*C07C 67/03* (2006.01)
*B01J 25/02* (2006.01)
*C07C 67/08* (2006.01)

(52) U.S. Cl.
CPC ............ *C07C 29/149* (2013.01); *B01J 23/72* (2013.01); *B01J 25/00* (2013.01); *B01J 25/02* (2013.01); *C07C 67/03* (2013.01); *C07C 67/08* (2013.01); *C07B 2200/07* (2013.01)

(58) Field of Classification Search
CPC .. B01J 23/72; B01J 25/00; B01J 25/02; C07C 29/149; C07C 67/03; C07C 67/08
USPC ........................................................ 560/179
See application file for complete search history.

(56) References Cited

U.S. PATENT DOCUMENTS

| | | | | |
|---|---|---|---|---|
| 2005/0182235 A1* | 8/2005 | Zhong | .................. | C07C 29/149 528/361 |
| 2011/0313211 A1* | 12/2011 | Schmidt | .................. | B01J 23/80 568/861 |
| 2014/0308719 A1* | 10/2014 | Clarke | ...................... | C12P 7/62 435/135 |

\* cited by examiner

*Primary Examiner* — Deborah D Carr
(74) *Attorney, Agent, or Firm* — William B. Miller

(57) ABSTRACT

A process is described for producing 1,3-butanediol, wherein an ester of poly-(R)-3-hydroxybutyrate such as formed by transesterification with an alcohol is reduced by hydrogenation in the presence of a skeletal copper-based catalyst to provide 1,3-butanediol. The 1,3-butanediol may be transesterified by reaction with additional poly-(R)-3-hydroxybutyrate ester to produce (R)-3-hydroxybutyl (R)-3-hydroxybutyrate.

10 Claims, No Drawings

PROCESS FOR PRODUCING 1,3-BUTANEDIOL AND FOR OPTIONALLY FURTHER PRODUCING (R)-3-HYDROXYBUTYL (R)-3-HYDROXYBUTYRATE

The present application is a continuation of U.S. Ser. No. 16/066,758 filed Jun. 28, 2018, which is a 371 National Phase Entry of International Patent Application PCT/US2016/65592 filed Dec. 8, 2016, which claims benefit of priority of U.S. Provisional Application No. 62/275,284, filed on Jan. 6, 2016, the contents of which are incorporated herein.

TECHNICAL FIELD

The present invention relates to processes for the manufacture of (R)-3-hydroxybutyl (R)-3-hydroxybutyrate (hereinafter, 3-HBR-3-HB).

BACKGROUND ART (R)-3-hydroxybutyl (R)-3-hydroxybutyrate, a ketone monoester, has recently been developed as a food additive, in particular, as a partial dietary carbohydrate replacement. WO 2014/140308 to Clarke et al. (WO'038) describes a process for the production of this material, which comprises: i) contacting poly-(R)-3-hydroxybutyrate with an alcohol to transesterify the poly-(R)-3-hydroxybutyrate and produce an ester of the alcohol and poly-(R)-3-hydroxybutyrate; ii) separating the product of step i) into a first and second portion and reducing the first portion of the poly-(R)-3-hydroxybutyrate ester to form (R)-1,3-butanediol; and iii) contacting under transesterification conditions the (R)-1,3-butanediol from step ii) with the second portion of the transesterified ester to produce (R)-3-hydroxybutyl (R)-3-hydroxybutyrate. The process described in WO'038 is offered as an improvement upon an earlier process described in WO 2010/120300, insofar as the earlier process was said to be based on costly starting materials and lower rates of reaction as compared to the process of WO'038.

In particular, the WO'038 process employs poly-(R)-3-hydroxybutyrate (CAS 625-72-9), described as a "relatively low cost starting material", as the feedstock. Poly-(R)-3-hydroxybutyrate (hereinafter, PHB) is one of the poly[(R)-3-hydroxyalkanoate] biodegradable and biocompatible thermoplastic materials that have been produced in recent years for a range of industrial and biomedical applications, and is commercially available. PHAs including PHB have been produced by a number of processes and by a number of companies, see, for example, U.S. Pat. No. 7,229,804 to Huisman et al. and the myriad references cited therein, see also US 2009/0018235 A1 to Nascimento et al. and Chaijamrus and Udpuay, "Production and Characterization of Polyhydroxybutyrate from Molasses and Corn Steep Liquor produced by *Bacillus megaterium* ATCC 6748", Agricultural Engineering International: the CIGR Ejournal, Manuscript FP 07 030, Vol. X, May 2008 and the various references cited therein. The PHB used for the WO'038 process is preferably obtained by fermentation of corn starch with microorganisms.

The process described in WO'038 produces (R)-1,3-butanediol from a first portion of an ester of PHB through a reduction step. As outlined in the WO'038 publication, the reduction may be accomplished by hydride transfer, hydrogenation, or hydrosilylation followed by silyl ether hydrolysis, though the reduction may generally be carried out with any suitable reducing agent for reducing a ketoester and may, for example, be enzyme-mediated.

The option for reduction by hydrogenation in the presence of a hydrogenation catalyst mentions Raney® nickel, "desirably employed at elevated pressure and temperature and catalysts comprising platinum, palladium, rhodium, iridium or ruthenium", though preferably the reduction is accomplished by a hydride transfer reagent and the sole working example correspondingly involves the use of sodium borohydride.

SUMMARY OF THE INVENTION

The use of sodium borohydride and similar hydride transfer reagents such as $LiAlH_4$, however, is undesirable at least from an environmental perspective. The WO'038 publication mentions hydrogenation as an alternative, but as mentioned provides no working examples thereof and no indication of how effective any particular catalyst would be for performing the reduction to 1,3-butanediol (1,3-BDO) nor of the conditions under which the reduction using a particular hydrogenation catalyst should be carried out.

The present invention in one aspect relates to a process for producing 1,3-butanediol from an ester of PHB, based upon the discovery that a skeletal copper catalyst is surprisingly much more effective for accomplishing the reduction of, for example, the ethyl ester of poly-(R)-3-hydroxybutyrate to provide (R)-1,3-butanediol than the one specific Raney® nickel hydrogenation catalyst mentioned in the WO'038 publication. The term "skeletal copper-based catalyst" as used herein means a porous catalytic alloy based material comprising copper and aluminum. The alloy in certain embodiments may further comprise small amounts of one or more additional metals added as promoters as further described hereafter, with common promoters including transition metals other than copper, for example, chromium, palladium, platinum, ruthenium, molybdenum, rhenium, manganese, nickel, zinc, zirconium, tungsten and combinations of two or more of these. When microscopically viewed as particulates, these high surface area, porous materials take on a skeletal appearance (sometimes also described as a "sponge like" appearance), having tortuous pore channels throughout. Skeletal copper catalysts of this character are well known, and have been manufactured and sold by W.R. Grace & Co. as part of a family of metal alloy-derived products under the RANEY® trademark.

In a further related aspect, the present invention concerns a process for producing (R)-3-hydroxybutyl (R)-3-hydroxybutyrate, which comprises: i) contacting poly-(R)-3-hydroxybutyrate with an alcohol to transesterify the poly-(R)-3-hydroxybutyrate and produce an ester of the alcohol and poly-(R)-3-hydroxybutyrate; ii) separating the product of step i) into a first and second portion and reducing the first portion of the poly-(R)-3-hydroxybutyrate ester through hydrogenation using a skeletal copper-based catalyst to form (R)-1,3-butanediol; and iii) contacting under transesterification conditions the (R)-1,3-butanediol from step ii) with the second portion of the transesterified ester to produce (R)-3-hydroxybutyl (R)-3-hydroxybutyrate.

DETAILED DESCRIPTION OF EMBODIMENTS

As used in this application, the singular forms "a", "an" and "the" include plural references unless the context clearly indicates otherwise. The term "comprising" and its derivatives, as used herein, are similarly intended to be open ended terms that specify the presence of the stated features, elements, components, groups, integers, and/or steps, but do not exclude the presence of other unstated features, elements, components, groups, integers and/or steps. This understanding also applies to words having similar meanings, such as the terms "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers, and/or steps. The term "consisting essentially of", as used herein, is intended to specify the presence of the stated features, elements, components, groups, integers, and/or steps, as well as those that do not materially affect the basic and novel characteristic(s) of stated features, elements, components, groups, integers, and/or steps.

Unless otherwise indicated, any definitions or embodiments described in this or in other sections are intended to be applicable to all embodiments and aspects of the subjects herein described for which they would be suitable according to the understanding of a person of ordinary skill in the art.

As indicated above, the present invention in one aspect concerns a process for making 1,3-butanediol in which a skeletal copper-based catalyst is used. More particularly, an ester formed from PHB by reaction with an alcohol is reduced by hydrogenation in the presence of such a skeletal copper-based catalyst. In a further, related aspect, the 1,3-butanediol thus made may be converted to (R)-3-hydroxybutyl (R)-3-hydroxybutyrate by contact with additional PHB under transesterification conditions.

Both promoted and base (unpromoted) skeletal copper-based catalysts have been sold commercially, but these may also be made as described in U.S. Pat. No. 8,735,635 to Schmidt ("Schmidt"), wherein conventional metallurgical techniques are used to first form a precursor alloy of copper and aluminum (optionally with small amounts included of up to 10 weight percent of the aforementioned promoter metal or metals) in which the copper is present in from 35 to 60 weight percent, with the remainder being primarily aluminum. The formed alloy is then crushed and/or ground and classified by passing it through a sieve to provide a material having a desired size. Larger particles exiting the grinding mechanism can be recycled for further grinding.

The formed alloy is then subjected to an aqueous alkali (e.g., sodium hydroxide) solution to extract the aluminum metal from the alloy. When a granular, fixed bed type catalyst is desired, typically being characterized by a cross-sectional diameter of from about 1 to 8 mm, the aluminum is partially extracted or leached, to the extent of leaching 20%-80%, preferably 40%-60%, and more preferably at least 50% of the aluminum originally present, to obtain a final catalyst composition with about 10 to 60, preferably 20 to 55 weight percent aluminum and the balance of copper and promoters if present. Processes for producing a porous copper-based catalyst in this manner are described by Schmidt as well known, having been previously described in U.S. Pat. Nos. 1,628,190; 1,915,473; 2,139,602; 2,461,396; and 2,977,327, all of which were referenced by Schmidt.

It is indicated that catalysts designed for a slurry reactor may be prepared in the same manner, except that the pre-leaching particles are less than 500 microns in size, more typically being less than 75 microns and frequently being in the range of from 10 to 50 microns, and except that typically the leaching of the particles is designed to leave lower aluminum amounts, for example, from 1% to 10% by weight of aluminum, and more desirably from 2% to 5% by weight of aluminum.

The alkali solution used to leach out the aluminum metal present is from either an inorganic or organic compound. Conventional processes utilize an aqueous solution having from about 2 to 35 weight percent of an alkali metal hydroxide (e.g., sodium hydroxide) employed as the leaching agent, typically using an aqueous solution of 5 to 10 weight percent of alkali metal hydroxide for forming a fixed bed catalyst as characterized above and a 20-30 weight percent solution for a slurry catalyst as characterized above. The alloy is usually treated at elevated temperatures of from 30 degrees Celsius to 110 degrees Celsius, typically using a temperature in the range of from 30 to 60 degrees Celsius for a fixed bed-type catalyst and a temperature between 60 and 100 degrees Celsius for a slurry-type catalyst.

Alloy particles being processed for fixed bed catalysts sit in a vessel through which the alkali solution is pumped and recirculated. For alloys processed for slurry use, the alkali solution is stirred and the alloy powder can be directly added therein, or an aqueous suspension of alloy powder can be prepared that is then mixed with the alkali solution. The aluminum in the alloy dissolves to form an alkali metal aluminate, e.g., sodium aluminate, with a vigorous evolution of hydrogen. The powder and alkali solution are in contact with one another until the aluminum content is reduced to the desired level, after which the leached alloy material is water-washed until the wash water has a slightly alkaline pH value in the range typically of from 8 to 9.

When promoter metals are used, Schmidt reports these are typically added for these skeletal copper-based catalysts as part of the starting alloy, but promoters can also be added in the leaching solution or in an impregnation or coating bath following the leaching of aluminum from the alloy particulate. Conventionally addition via the leaching solution is accomplished by inclusion in the leaching solution of a suitable promoter precursor, for example, a chloride salt, while addition post-leaching typically involves surface deposition by contact with a usually alkaline pH salt solution in a washing step. A coating or plating technique as described in U.S. Pat. No. 7,375,053 is also indicated in Schmidt as useful.

In the context of the present invention according to a first aspect, an ester of poly-(R)-3-hydroxybutyrate is hydrogenated using a skeletal copper-based catalyst to form (R)-1,3-butanediol. The ester of PHB used as a feedstock can be formed from any alcohol which allows the ester of PHB to be efficiently reduced to 1,3-butanediol. Suitably a dihydric or trihydric alcohol may be employed, but preferably a monohydric alcohol, for example, a $C_1$-$C_6$ monohydric alcohol, is used. The ethyl ester of PHB is a preferred starting material, especially in the further context of forming (R)-3-hydroxybutyl (R)-3-hydroxybutyrate by transesterifying the 1,3-butanediol with additional PHB, as ethanol is inexpensive and readily available and particularly as any ethanol remaining with the 1,3-butanediol following the reduction of the ester of PHB and purification of the reduction product (as described hereafter) will in the context of this further aspect be accepted as not posing a hazard for human consumption, in the manufacture of (R)-3-hydroxybutyl (R)-3-hydroxybutyrate as a food additive.

The transesterification of PHB to provide this ester of PHB as a starting material is suitably carried out with typically an excess of the alcohol (e.g., with from 2 to 6 parts by weight of alcohol per part of PHB) under acidic conditions, for example, where an acid catalyst is employed. The acid catalyst may be organic or inorganic, and solid acid catalysts may be used as well, but preferably will be a mineral acid such as sulfuric acid. The transesterification is carried out at elevated temperature, preferably at a temperature greater than 50 degrees Celsius, in other embodiments at a temperature preferably greater than 90 degrees Celsius and in still other embodiments at a temperature of greater than 150 degrees Celsius. Elevated pressure may be employed. The reaction time can be at least 1 hour, but will preferably be on the order of at least 10 hours, especially 15 to 30 hours.

Upon the completion of the transesterification step, the product mixture from the transesterification can be further processed by filtering and other means for purification, for example, by neutralization of the acid with addition of a base such as hydroxide, bicarbonate and acetate, especially calcium hydroxide or sodium bicarbonate, followed by distillation to remove excess alcohol and byproducts of the reaction. Typically the distillation is carried out in multiple stages under atmospheric pressure and at temperatures above the boiling point of the alcohol to isolate the ester of PHB for the subsequent hydrogenation step.

Under preferred temperatures and pressures for carrying out the hydrogenation, the ester of PHB will be in liquid form and the hydrogen will be in gaseous form, so that any conventionally known mode or method for carrying out a gas/liquid reaction in the presence of a solid catalyst can be contemplated. Preferably, a fixed catalyst bed arrangement is used for carrying out the hydrogenation as a continuous process, wherein a mass of the catalyst is packed in a constrained static bed within the reactor and the reactants move through the catalyst bed. The catalyst used in such an arrangement can take various forms, including, but not being limited to, pressed cylinders, tablets, lozenges, wagon wheels, rings, stars, or extrudates such as solid extrudates, polylobal extrudates, hollow extrudates and honeycomb bodies.

In certain embodiments, reaction temperatures for the hydrogenation are from 120 to 220 degrees Celsius, with liquid hourly space velocities ranging from 0.1 $hr^{-1}$ to 2 $hr^{-1}$, and hydrogen supply pressures ranging from 5.5 MPa, gauge (800 pounds per square inch, gauge) to 17.2 MPa, gauge (2500 pounds per square inch, gauge).

In other embodiments, the reaction temperature can range from 150 to 220 degrees Celsius, with hydrogen supply pressures ranging from 8.3 MPa, gauge (1200 psig) to 12.4 MPa, gauge (1800 psig), and liquid hourly space velocities ranging from 0.2 $hr^{-1}$ to 1 $hr^{-1}$.

In still other embodiments, the reaction temperature is from 160 to 200 degrees Celsius, with hydrogen supply pressures of from 9.7 MPa, gauge (1400 psig) to 12.4 MPa, gauge (1800 psig), and liquid hourly space velocities ranging from 0.4 $hr^{-1}$ to 0.8 $hr^{-1}$.

Preferably the amount of butanol produced in the hydrogenation is low, the selectivity to butanol preferably being not more than 5 mol percent, especially not more than 3 mol percent, and particularly not more than 2 mol percent.

Conversely, preferably the selectivity to the desired 1,3-butanediol product will be at least 30 mol percent, more preferably will be at least 40 mol percent and still more preferably will be at least 50 mol percent.

Recovery of the 1,3-butanediol product following the hydrogenation step can involve further treatment to remove catalyst particles, unreacted starting materials and byproducts, for example, by filtration, distillation and the like.

In a second aspect, the present invention relates to a process for producing (R)-3-hydroxybutyl (R)-3-hydroxybutyrate, which comprises: i) contacting poly-(R)-3-hydroxybutyrate with an alcohol to transesterify the poly-(R)-3-hydroxybutyrate and produce an ester of the alcohol and poly-(R)-3-hydroxybutyrate; ii) separating the product of step i) into a first and second portion and reducing the first portion of the poly-(R)-3-hydroxybutyrate ester through hydrogenation using a skeletal copper-based catalyst to form (R)-1,3-butanediol; and iii) contacting under transesterification conditions the (R)-1,3-butanediol from step ii) with the second portion of the transesterified ester to produce (R)-3-hydroxybutyl (R)-3-hydroxybutyrate. Accordingly, after transesterifying PHB with an alcohol to produce an ester of PHB as outlined above, a portion of the resultant ester is set aside while a second portion is hydrogenated as has been described, and then the resultant 1,3-butanediol and the first portion of PHB ester are combined and transesterified, for example, as in forming the PHB ester, to provide the (R)-3-hydroxybutyl (R)-3-hydroxybutyrate. The (R)-3-hydroxybutyl (R)-3-hydroxybutyrate may again be further processed, for example, by filtering, distillation and like well-known purification techniques, as needed.

The present invention is more particularly illustrated by the following, non-limiting examples:

Examples 1-3

A commercial Raney® copper catalyst was loaded into a 30 cubic centimeter fixed bed reactor, and hydrogen was thereafter supplied to the reactor at the pressures indicated in Table 1 below at a rate of 0.8 liters per minute, together with a neat liquid feed of ethyl-3-hydroxybutyrate (CAS 5405-41-4) from WILD Flavors, Inc. The products achieved from hydrogenating the ethyl-3-hydroxybutyrate at several reactor temperatures and the indicated liquid hourly space velocities are summarized in Table 1.

TABLE 1

Reaction conditions and product yield

| Reaction condition | | | | Product mixture (mol %) | | |
|---|---|---|---|---|---|---|
| Temp. (° C.) | LHSV ($hr^{-1}$) | H$_2$ Pressure in MPa, gauge (psig) | H$_2$ Flow (L/min) | 1,3-BDO | Ethyl 3-hydroxy-butyrate | Butanol |
| 180 | 0.4 | 12.4 (1800) | 0.8 | 10 | 90 | ND |
| 200 | 1 | 13.1 (1900) | 1.0 | 43 | 52 | <5% |
| 193 | 0.6 | 13.5 (1960) | 0.8 | 48 | 50 | <2% |

Comparative Example 1

For comparison, a commercial Raney® nickel catalyst from the same manufacturer was loaded into the same 30 cubic centimeter fixed bed reactor, and used to hydrogenate a neat ethyl-3-hydroxybutyrate feed under the same reaction conditions as in the 193 degree Celsius reactor temperature run in Table 1. The results are shown in Table 2 compared to the results obtained using the Raney® copper catalyst.

TABLE 2

Ethyl-3-hydroxybutyrate hydrogenation with different Raney ® catalysts

| | Product mixture (mol %) | | |
|---|---|---|---|
| Catalyst | 1,3-BDO | Ethyl 3-hydroxybutyrate | Butanol |
| Raney ® Nickel | 17 | 81 | <1% |
| Raney ® Copper | 48 | 50 | <2% |

Example 4 and Comparative Example 2

Because the Raney® copper catalyst did perform differently at different reactor temperatures, and appeared to have performed better at 193 degrees Celsius as compared to either 180 degrees Celsius or 200 degrees Celsius, a further comparison was made to a Raney® nickel catalyst at a second, lower temperature of 175 degrees Celsius. The same 30 cc fixed bed reactor was used, with a hydrogen pressure of 13.5 MPa, gauge (1960 psig), an LHSV of 0.6 $hr^{-1}$ and a hydrogen flowrate of 0.8 liters/minute. The results are shown in Table 3, expressed in weight percents this time.

TABLE 3

Ethyl-3-hydroxybutyrate hydrogenation with different catalysts

| Catalyst | Product mixture (weight %) | | |
| --- | --- | --- | --- |
| | 1,3-BDO | Ethyl 3-hydroxybutyrate | Butanol |
| Raney ® Nickel | 12 | 72 | 1.4 |
| Raney ® Copper | 29 | 57 | 1.3 |

Example 5

After distilling to remove ethanol and butanol, to twenty grams of remaining product from the hydrogenation of ethyl-3-hydroxybutyrate using a skeletal copper-based catalyst in a 100 mL round bottomed flask, were added 0.2 grams of scandium triflate, $Sc(OTf)_3$. The solution was stirred at 100 degrees Celsius for 18 hours under house vacuum. After 18 hours, the stirring was stopped and the flask contents were allowed to cool down to room temperature, then water-washed once and ethyl acetate-washed twice with 30 mL increments. The organic layer that formed upon settling was collected and dried with $Na_2SO_4$, then distilled sequentially to successfully obtain 3-hydroxybutyl-3-hydroxybutyrate.

Example 6

After distilling to remove ethanol and butanol, to twenty grams of remaining product from the hydrogenation of ethyl-3-hydroxybutyrate using a skeletal copper-based catalyst in a 100 mL round bottomed flask, were added 0.2 grams of p-toluenesulfonic acid. The solution was stirred at 100 degrees Celsius for 18 hours under house vacuum. After 18 hours, the stirring was stopped and the flask contents were allowed to cool down to room temperature, then water-washed once and ethyl acetate-washed twice with 30 mL increments. The organic layer that formed upon settling was collected and dried with $Na_2SO_4$, then distilled sequentially to successfully obtain 3-hydroxybutyl-3-hydroxybutyrate.

What is claimed is:

1. A process for producing 1,3-butanediol, comprising contacting an ester of poly-(R)-3-hydroxybutyrate with a source of hydrogen in the presence of a skeletal copper-based catalyst under elevated temperature conditions, wherein the term ester of poly-(R)-3-hydroxybutyrate refers to an ester formed by reaction of poly-(R)-3-hydroxybutyrate with an alcohol and wherein the term skeletal copper-based catalyst refers to a porous catalytic alloy based material comprising copper and aluminum.

2. The process of claim 1, wherein the ester of poly-(R)-3-hydroxybutyrate is a methyl, ethyl, propyl, butyl, pentyl or hexyl ester.

3. The process of claim 2, wherein the ethyl ester is used.

4. The process of any one of claims 1-3, wherein the process is conducted continuously, using a fixed catalyst bed.

5. The process of claim 4, wherein the skeletal copper-based catalyst is a promoted or unpromoted copper-aluminum alloy catalyst containing from 10 to 60 weight percent of aluminum and with the balance consisting of copper and any promoters present.

6. The process of claim 5, wherein the catalyst contains from 20 to 55 weight percent of aluminum.

7. The process of claim 1, conducted at a reactor temperature between 120 degrees Celsius and 220 degrees Celsius, a liquid hourly space velocity of from 0.1 $hr^{-1}$ to 2 $hr^{-1}$ and a hydrogen supply at a pressure of from 5.5 MPa, gauge to 17.2 MPa, gauge.

8. The process of claim 7, conducted at a reactor temperature between 150 degrees Celsius and 220 degrees Celsius, a liquid hourly space velocity of from 0.2 $hr^{-1}$ to 1 $hr^{-1}$ and a hydrogen supply at a pressure of from 8.3 MPa, gauge to 12.4 MPa, gauge.

9. The process of claim 8, conducted at a reactor temperature between 160 degrees Celsius and 200 degrees Celsius, a liquid hourly space velocity of from 0.2 $hr^{-1}$ to 1 $hr^{-1}$ and a hydrogen supply at a pressure of from 9.7 MPa, gauge to 12.4 MPa, gauge.

10. A process for producing (R)-3-hydroxybutyl (R)-3-hydroxybutyrate, comprising:
    contacting poly-(R)-3-hydroxybutyrate with an alcohol under transesterification conditions for transesterifying the poly-(R)-3-hydroxybutyrate and producing an ester of the alcohol and poly-(R)-3-hydroxybutyrate;
    separating the product of the transesterification step into first and second portions comprising the ester of the alcohol and poly-(R)-3-hydroxybutyrate;
    reducing the first portion of the poly-(R)-3-hydroxybutyrate ester through a process according to any one of claims 1-9 to produce 1,3-butanediol;
    contacting the 1,3-butanediol with the second portion of the poly-(R)-3-hydroxybutyrate ester under transesterification conditions for producing (R)-3-hydroxybutyl (R)-3-hydroxybutyrate.

* * * * *